US00PP11960P2

(12) United States Plant Patent
van Veen

(10) Patent No.: US PP11,960 P2
(45) Date of Patent: Jun. 26, 2001

(54) ASTILBE PLANT NAMED 'TOUCH OF PINK'

(75) Inventor: Wim van Veen, Noorden (NL)

(73) Assignee: Future Plants V.O.F., Noordwijk (NL)

( * ) Notice: Subject to any disclaimer, the term of this patent is extended or adjusted under 35 U.S.C. 154(b) by 0 days.

(21) Appl. No.: 09/473,564

(22) Filed: Dec. 29, 1999

(51) Int. Cl.[7] ..... A01H 5/00

(52) U.S. Cl. ..... Plt./263
(58) Field of Search ..... Plt./263

*Primary Examiner*—Bruce R. Campell
*Assistant Examiner*—Kent L. Bell
(74) *Attorney, Agent, or Firm*—C. A. Whealy

(57) ABSTRACT

A distinct cultivar of Astilbe plant named 'Touch of Pink', characterized by its upright and compact plant habit; durable dark green leaves; very freely, uniformly and continuous flowering; and attractive light pink-colored flowers.

2 Drawing Sheets

BACKGROUND OF THE INVENTION

The present invention relates to a new and distinct cultivar of Astilbe plant, botanically known as Astilbe hybrid, and hereinafter referred to by the cultivar name 'Touch of Pink'.

The new cultivar is a peoduct of a planned breeding program conducted by the Inventor in Noorden, The Netherlands. The objective of the breeding program was to develop new freely-flowering compact Astilbe cultivars.

The new cultivar originated from a cross made by the Inventor in 1992 of the *Astilbe simplicifolia* cultivar 'Hennie Graafland', not patented, as the male or pollen parent, with the *Astiebe japonica* cultivar 'Europa', not patented, as the female or seed parent.

The cultivar 'Touch of Pink' was discovered and selected by the Inventor as a flowering plant within the progeny of the stated cross in a controlled environment in Noorden, The Netherlands.

Asexual propagation of the new cultivar by divisions harvested at Noorden, The Netherlands, has shown that the unique features of this new Astilbe are stable and reproduced true to type in successive generations.

SUMMARY OF THE INVENTION

Plants of the cultivar 'Touch of Pink' have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Touch of Pink'. The characteristics in combination distinguish 'Touch of Pink' as a new and distinct cultivar:

1. Upright and compact plant habit.
2. Durable dark green leaves.
3. Very freely, uniformly and continuous flowering.
4. Attractive light pink-colored flowers.

Plants of the new Astilbe differ from plants of the male parent, the cultivar 'Hennie Graafland', in flower shape, in addition, plants of the new Astilbe are narrower and are move floriferous than plants of the cultivar 'Hennie Graafland'.

Plants of the new Astilbe differ from plants of the female parent, the cultivar 'Europa', in leaf shape and flower color, in addition, plants of the new Astilbe are more compact than plants of the cultivar 'Europa'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Astilbe.

The photograph on the first sheet comprises a side perspective view of typical plants of the new Astilbe.

The photograph at the top of the second sheet comprises a close-up view of a typical inflorescence of the new Astilbe.

The photograph at the bottom of the second sheet comprises a close-up view of a typical leaf of the new Astilbe.

DETAILED BOTANICAL DESCRIPTION

In the following description, color references are made to The Royal Horticultural Society Colour Chart except where general terms of ordinary dictionary signiticance are used. Plants used for the description were about one year-old and grown in 17-cm containers under outdoor production conditions which closely approximate commercial production conditions during the spring and summer in Noorden, The Netherlands.

Botanical classification: Astilbe hybrid cultivar 'Touch of Pink'.

Parentage:

*Female parent.*—*Astilbe japonic* cultivar 'Europa', not patented.

*Male parent.*—*Astilbe simplicifolia* cultivar 'Hennie Graafland', not patented.

Propagation:

*Type.*—By root divisions.

*Time to rooting.*—About 3 months at temperatures about 18° C.

*Root description.*—Fine.

Plant description:

*Crop time.*—From divisions, about 40 weeks are required to produce fully-grown flowering plants in 17-cm containers.

*Form*.—Upright, compact; inverted triangle.

*Branching habit*.—Flowering stems and leaves arise from the roots.

*Plant height*.—About 35 cm.

*Area of spread*.—About 25 cm.

*Vigor*.—Moderate.

*Stems*.—Length: About 35 cm. Internode length: About 4 cm. Texture: Very sparsely covered with very short (less the 0.5 mm) brown hairs. Color: 137A to 176A.

*Foliage description*.—Arrangement: Bi-ternately compound; alternate. Quantity of leaflets per leaf: Typically about 27. Leaf length, including petiole: About 20 cm. Leaf width: About 14 cm. Leaflet length: About 2.5 cm. Leaflet width: About 2 cm. Leaflet shape: Ovate to elliptic. Leaflet apex: Acuminate to acute. Leaflet base: Rounded. Leaflet margin: Serrate, occasionally doubly serrate. Leaflet texture: Slightly lustrous; lower surface very sparsely covered with very short (less that 0.5 mm) brown hairs concentrated along the medvein. Leaflet color: Young and mature foliage, upper surface: 137A. Young and mature foliage, lower surface: 137C. Venation, upper surface: 137A. Venation, lower surface: 138C. Petiole: Length: About 10 cm. Diameter: About 1.75 mm. Texture: Very sparsely covered with very short (less than 0.5 mm) brown hairs. Color: 137A to 176A.

Flower description:

*Flower type and habit*.—Numerous small single flowers arranged in branched panicles. Very freely flowering with obout 3,500 flowers and flower buds per plant. Flowers sessile.

*Natural flowering season*.—Continuously flowering typically during the early summer.

*Flower longevity*.—Flowers last a few weeks on the plant and more than one week as a cut flower. Flowers persistent.

*Fragrance*.—Faint musty odor, not unpleasant.

*Flower buds*.—Length: About 2 mm. Diameter: About 1 mm. Shape: Orbicular. Rate of opening: About three weeks from visible bud to fully opened flower. Color: 62D to 138D.

*Flower size*.—Length (height): About 3 mm. Diameter: About 3 mm.

*Petals*.—Arrangement: Five. Shape: Linear to linear-oblanceolate. Apex: Obtuse. Margin: Entire. Length: About 3 mm. width: About 0.5 mm. Texture: Smooth. Color: When opening, upper and lower surfaces: 65D. Fully opened flower, upper and lower surfaces: 65A to 65B.

*Calyx*.—Length: About 3 mm. Width: About 3 mm. Number of sepals: About five. Sepal Shape: Ovate. Sepal apex: Obtuse. Sepal margin: Entire. Sepal color (Both surfaces): Close to 62D to 69D.

*Reproductive organs*.—Stamens: Stamen number: About ten. Anther attachment: Basifixed. Anther length: Less than 0.5 mm. Anther color: Creamy white. Pollen amount: Scarce. Pollen color: Creamy white. Pistils: Pistil number: Two. Pistil length: About 1.75 mm. Stigma shape: Club-shaped. Stigma color: Pale pinkish green. Style length: About 1.25 mm. Style color: Pale pinkish green. Ovary color: Pale pinkish green.

*Seed*.—Length: Less than 0.5 mm. Diameter: Less than 0.5 mm. Color: Light brown.

Disease resistance: Under commercial conditions, plants of the Astilbe are slightly susceptible to diseases common to Astilbe.

It is claimed:

1. A new and distinct cultivar of Astilbe plant named 'Touch of Pink', as illustrated and described.

* * * * *

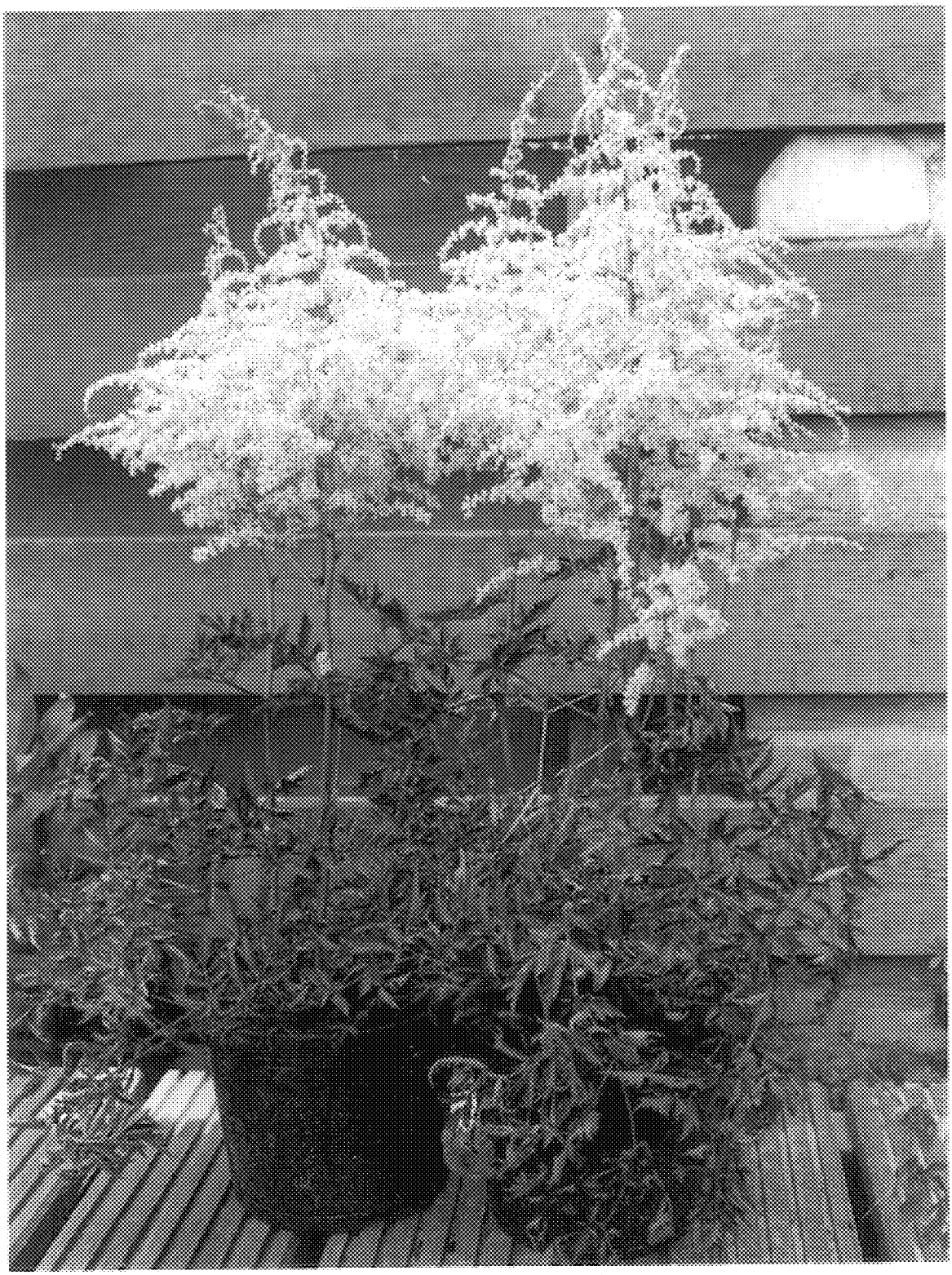

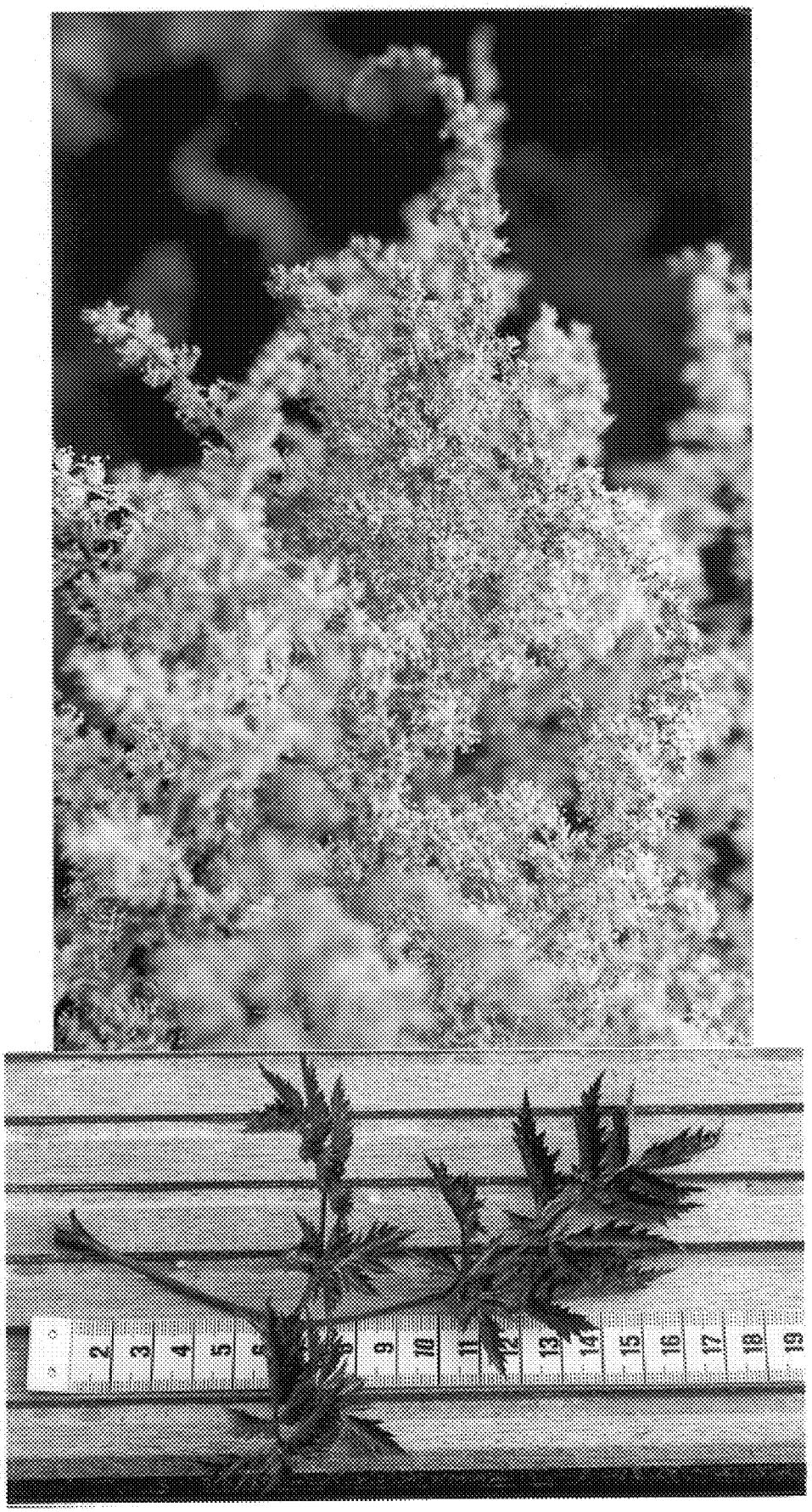
2
3
4
5
6
7
8
9
10
11
12
13
14
15
16
17
18
19